United States Patent
Parker

(10) Patent No.: US 8,167,974 B2
(45) Date of Patent: May 1, 2012

(54) TEREPHTHALIC ACID PURGE FILTRATION RATE BY CONTROLLING % WATER IN FILTER FEED SLURRY

(75) Inventor: Kenny Randolph Parker, Afton, TN (US)

(73) Assignee: Grupo Petrotemex, S.A. De C.V., San Pedro Garza Garcia (MX)

( * ) Notice: Subject to any disclaimer, the term of this patent is extended or adjusted under 35 U.S.C. 154(b) by 0 days.

(21) Appl. No.: 12/860,135

(22) Filed: Aug. 20, 2010

(65) Prior Publication Data

US 2012/0042752 A1 Feb. 23, 2012

(51) Int. Cl.
  *C22B 3/44* (2006.01)
(52) U.S. Cl. .................. 75/721; 75/739; 502/22
(58) Field of Classification Search .......... 75/721, 75/739; 502/22–33
  See application file for complete search history.

(56) References Cited

U.S. PATENT DOCUMENTS

| | | | | |
|---|---|---|---|---|
| 4,939,297 A | * | 7/1990 | Browder et al. | 562/485 |
| 7,282,151 B2 | * | 10/2007 | Parker et al. | 210/634 |
| 7,956,215 B2 | * | 6/2011 | Gibson et al. | 562/414 |
| 2002/0193630 A1 | * | 12/2002 | Lin et al. | 562/414 |
| 2004/0249208 A1 | * | 12/2004 | Lin et al. | 562/600 |

OTHER PUBLICATIONS

International Search Report and Written Opinion of the International Searching Authority issued Sep. 9, 2011, in PCT/US11/47500.

* cited by examiner

*Primary Examiner* — George Wyszomierski
*Assistant Examiner* — Tima M McGuthry Banks
(74) *Attorney, Agent, or Firm* — Oblon, Spivak, McClelland, Maier & Neustadt, L.L.P.

(57) ABSTRACT

The process relates improving the recovery of a metal catalyst from an oxidizer purge stream produced in the synthesis of carboxylic acid, typically terephthalic acid, while utilizing pressure filtration.

24 Claims, 3 Drawing Sheets

TEREPHTHALIC ACID PURGE FILTRATION RATE BY CONTROLLING % WATER IN FILTER FEED SLURRY

FIELD OF INVENTION

This invention relates to improving the recovery of a metal catalyst from an oxidizer purge stream produced in the synthesis of terephthalic acid. The improved catalyst recovery is accomplished in a purge process comprising evaporative concentration of an oxidizer purge feed to generate a super concentrated purge slurry, addition of water to the super concentrated purge slurry to generate a water rich super concentrated purge slurry, filtration of the water rich super concentrated purge slurry to generate a mother liquor and a filter cake, and routing the mother liquor to an extraction zone.

BACKGROUND OF THE INVENTION

Terephthalic acid is commercially produced by oxidation of paraxylene in the presence of a catalyst, such as, for example, Co, Mn, Br and a solvent. Terephthalic acid used in the production of polyester fibers, films, and resins must be further treated to remove impurities formed as a result of the oxidation of paraxylene.

Terephthalic acid (TPA) is an intermediate in the production of polyesters for plastics and fiber applications. Commercial processes for the manufacture of TPA are often based on the heavy-metal catalyzed oxidation of p-xylene, generally with a bromide promoter in an acetic acid solvent. Due to the limited solubility of TPA in acetic acid under practical oxidation conditions, a slurry of TPA crystals is usually formed in the oxidation reactor. Typically, the TPA oxidizer slurry is withdrawn from the reactor and TPA solids are separated from the oxidizer mother liquor using conventional solid-liquid separation techniques. The oxidizer mother liquor, which contains most of the catalyst and promoter used in the process, is recycled to the oxidation reactor. Aside from the catalyst and promoter, the oxidizer mother liquor stream also contains dissolved TPA and many by-products and impurities. These by-products and impurities arise partially from minor impurities present in the p-xylene feed stream. Other impurities arise due to the incomplete oxidation of p-xylene resulting in partially oxidized products. Still other by-products result from competing side reactions formed as a result of the oxidation of p-xylene to terephthalic acid. Patents disclosing the production of terephthalic acid such as U.S. Pat. No. 4,158,738 and U.S. Pat. No. 3,996,271 are hereby incorporated by reference in their entirety to the extent that they do not contradict statements herein.

The TPA solids undergo a solid-liquid separation wherein fresh solvent is utilitized to displace a major portion of the liquid component of the oxidizer mother liquor.

Many of the impurities in the oxidizer mother liquor stream that are recycled are relatively inert to further oxidation. Such impurities include, for example, isophthalic acid, phthalic acid and trimellitic acid. Impurities, which may undergo further oxidation are also present, such as, for example, 4-carboxybenzaldehyde, p-toluic acid and p-tolualdehyde. Oxidation inert impurities tend to accumulate in the oxidizer mother liquor upon recycle. The concentration of these inert impurities will increase in the oxidizer mother liquor until an equilibrium is reached whereby the rate of removal of each impurity via the TPA product balances with the rate of formation and the rate of addition to the oxidation process. The normal level of impurities in commercial crude TPA makes it unsuitable for direct use in most polymer applications.

Conventionally, crude TPA has been purified either by conversion a dimethyl ester or by dissolution in water with subsequent hydrogenation over standard hydrogenation catalysts. More recently, secondary oxidative treatments have been used to produce polymer-grade TPA. It is desirable to minimize the concentration of impurities in the mother liquor and thereby facilitate subsequent purification of TPA. In some cases, it is not possible to produce a purified, polymer-grade TPA unless some means for removing impurities from the oxidizer mother liquor stream is utilized.

One technique for impurity removal from a recycle stream commonly used in the chemical processing industry is to draw out or "purge" some portion of the oxidation mother liquor recycle stream. Typically, the purge stream is simply disposed of or, if economically justified, subjected to various treatments to remove undesired impurities while recovering valuable components. One example is U.S. Pat. No. 4,939,297 herein incorporated by reference in their entirety to the extent that they do not contradict statements herein. The amount of purge required for control of impurities is process-dependent; however, a purge amount equal to 10-40% of the total oxidizer mother liquor stream is usually sufficient to produce TPA adequate as feedstock for commercial polymer manufacture. In the production of TPA, the percentage purge of the oxidizer mother liquor stream purge necessary to maintain acceptable impurity concentrations, coupled with the economic value of the metal catalyst and solvent components in the oxidizer purge stream, make simple disposal of the oxidizer purge stream economically unattractive. Thus, there is a need for a process that recovers essentially all of the valuable metal catalysts and acetic acid contained in the oxidizer purge stream while removing a major portion of the impurities present in the oxidizer purge stream. The metal catalyst can be recovered in an active form suitable for reuse by direct recycling to the p-xylene oxidation step.

A number patents teach a terephthalic acid process comprising a purge process comprising concentration, filtration, followed by extraction.

In such purge processes, oxidation by-products exit the process in two locations. Oxidation by-products that come out of solution in the purge concentration zone due to solvent loss are isolated and washed in a subsequent filtration zone to generate an oxidation by-product rich wet cake which can exit the process. Also, those oxidation by-products that remain in solution after the concentration zone pass through the filtration zone in the liquid mother liquor which is then routed to an extraction and distillation zone where oxidation by-products are concentrated into a waste sludge stream suitable for exiting the process. It is desirable to minimize the catalyst content in the oxidation by-product wet cake generated in the filtration zone as well as the oxidation by-product sludge stream generated in the extraction and distillation zone. Any catalyst present in these two streams will not be routed back to the p-xylene oxidation reactor and will therefore represent a loss of catalyst in the terephthalic acid process.

Water is added to the purge filter mother liquor in a mix zone just prior to extraction, generating a stream that is a mixture of mother liquor and water. The purpose of adding water to the purge filter mother liquor just prior to the extraction zone is to adjust the water:acid ratio for acceptable performance in the extraction zone. We have discovered that splitting this water stream and routing a portion of it to a mix zone immediately before the purge filter where the water is mixed with concentrated filter feed just prior to filtration has a material impact on decreasing the cobalt content in the purge filter wet cake generated in the purge filtration zone. It should be noted that splitting the water stream normally added just prior to extraction and routing a portion of the water stream to the filter feed just prior to filtration does not impact the water:acid ratio of the purge filter mother liquor and water mixture routed to extraction because any water added prior to filtration simply passes through the filtration zone with the filtration mother liquor.

SUMMARY OF THE INVENTION

This invention relates to removal of impurities and the recovery of a metal catalyst from an oxidizer purge stream produced in the synthesis of carboxylic acids, typically terephthalic acid, the process comprising:
(a) subjecting an oxidizer purge stream formed in a terephthalic acid process to evaporation in a 1st evaporator zone to produce a $1^{st}$ vapor stream and a concentrated purge stream; wherein the oxidizer purge stream comprises a carboxylic acid, a metal catalyst, impurities, water and a solvent; wherein the solvent comprises acetic acid and
(b) adding water to the concentrated purge stream in a $1^{st}$ mixing zone to produce a water rich concentrated purge stream;
(c) subjecting the water rich concentrated purge stream to evaporation in a $2^{nd}$ evaporator zone to produce a $2^{nd}$ vapor rich and a super concentrated purge slurry stream; and
(d) adding water to a super concentrated purge slurry in a $2^{nd}$ mix zone to produce a water rich super concentrated purge slurry, and
(e) filtering the water rich super concentrated purge slurry in a solid-liquid separation zone to form a filter cake and mother liquor
(f) washing the filter cake with a wash feed in the solid-liquid separation zone to form a washed filter cake, and wash liquor
(g) adding water to the mother liquor in a $3^{rd}$ mix zone to recover the metal catalyst and then subjecting an aqueous mixture so formed to extraction with an extraction solvent to produce an extract stream and a raffinate stream comprising a metal catalyst.

These embodiments and other embodiments and other embodiments will become more apparent to others with ordinary skill in the art after reading this disclosure.

DESCRIPTION OF THE INVENTION

In this specification and in the claims, which follow, reference will be made to a number of terms which shall be defined to have the following meanings:

As used in the specification and the appended claims, the singular forms "a," "an" and "the" include plural referents unless the context clearly dictates otherwise. Thus, for example, reference to a pipe reactor includes one or more pipe reactors.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where the event or circumstance occurs and instances where it does not. For example, the phrase "optionally heated" means that the material may or may not be heated and that such phrase includes both heated and unheated processes.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the appended claims, the use of "percent" or "%" refers to a weight percent.

Figure 1:
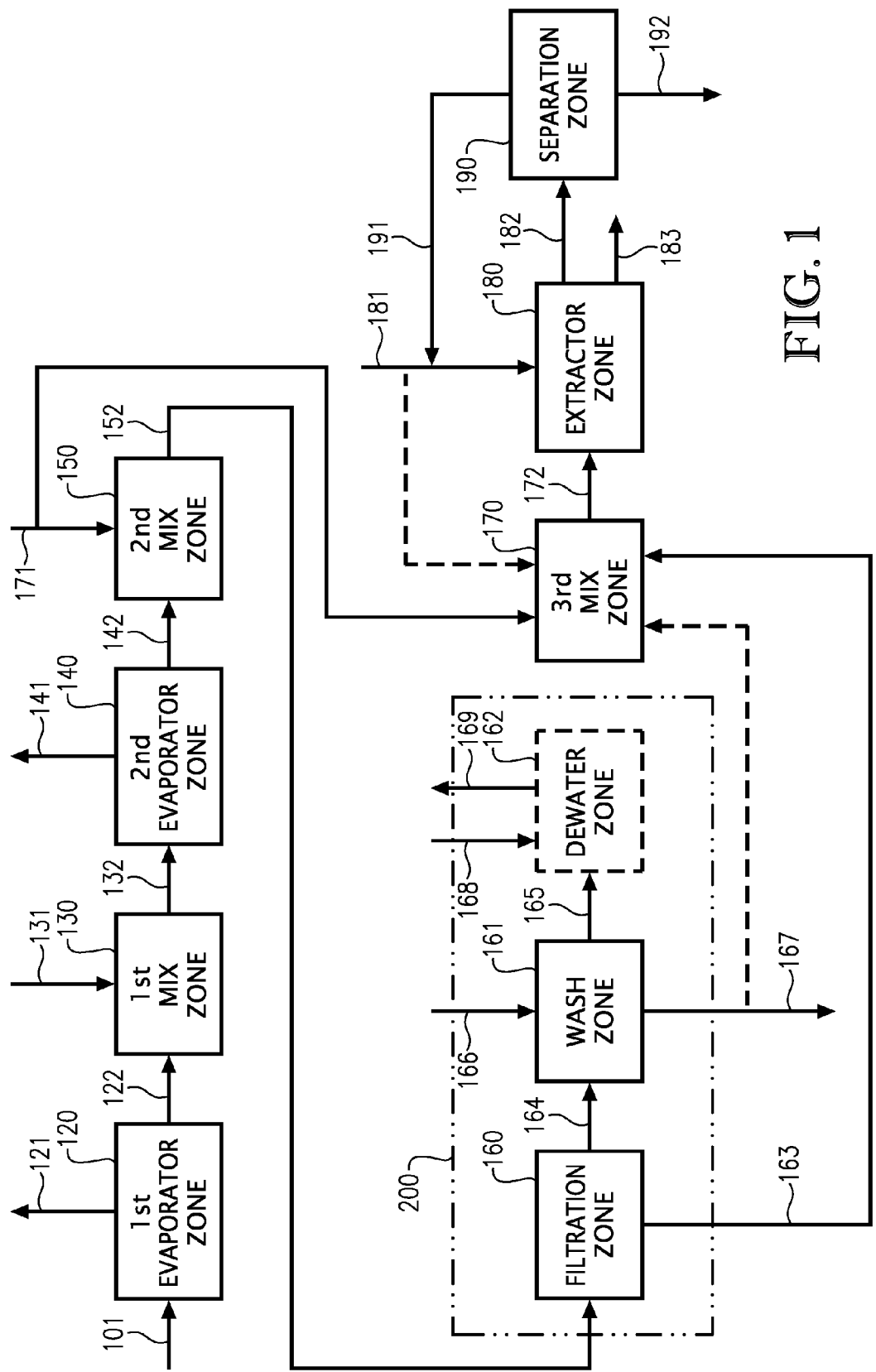
FIG. 1 illustrates an embodiment of the invention wherein a method for removing impurities from an oxidizer purge stream formed in a terephthalic acid process comprising acetic acid, water, a metal catalyst, and oxidation impurities by (a) evaporating a portion of an oxidizer purge stream in a first evaporator zone to produce a concentrated purge stream and a $1^{st}$ vapor stream comprising acetic acid and water (b) adding water in a controlled fashion to the concentrated purge stream in a $1^{st}$ mixing zone to produce a water rich concentrated purge stream (c) evaporating a portion of water rich concentrated purge stream in a $2^{nd}$ evaporator zone to form a super concentrated purge slurry stream with a water content ranging from 5.8 wt % to 24.4 wt % and a $2^{nd}$ vapor stream comprising acetic acid and water (d) adding water to the super concentrated purge slurry stream in a $2^{nd}$ mixing zone to produce a water rich super concentrated purge slurry stream; (e) separating solids from the water rich super concentrated purge slurry stream and subjecting the solids to a wash feed in a solid-liquid separation zone to form a mother liquor stream, a wash liquor stream, and a washed filter cake stream; (f) mixing in a $3^{rd}$ mixing zone water with the mother liquor stream and optionally a portion of the wash liquor stream to form an aqueous mixture; and (g) adding an extraction solvent to the aqueous mixture in an extraction zone to form an extract stream and a raffinate stream; and (h) feeding the extract stream to a distillation column to form an extraction solvent recycle stream and a sludge stream.

In one embodiment of this invention, a process to remove oxidation by-product impurities from an oxidizer purge stream 101 is provided as shown in FIG. 1. The process comprises the following steps.

Step (a) comprises subjecting an oxidizer purge stream 101 to evaporation in a first evaporator zone 120 to produce a $1^{st}$ vapor stream 121 and a concentrated purge stream 122.

The oxidizer purge stream 101 is withdrawn from a carboxylic acid oxidative synthesis process comprising terephthalic acid. One method for generating oxidizer purge stream 101 is to filter terephthalic acid oxidizer slurry and collect a portion of the mother liquor exiting the filter and routing it to the purge process. Yet another method for generating oxidizer purge stream 101 is to conduct a solvent swap on terephthalic acid oxidation slurry displacing a portion of the oxidation mother liquor and routing it to the purge process. The oxidation mother liquor obtained from a terephthalic acid process can be cooled to a temperature ranging from 90° C. to 45° C. and routed it to a clarification pressure filter such as a candle filter to remove any solids present before routing it to the $1^{st}$ evaporator in the purge process.

The oxidizer purge stream 101 serves as the feed stream to the present terephthalic acid purge process. The oxidizer purge stream 101 comprises carboxylic acid, water, a solvent, the metal catalyst and impurities. The impurities comprise organic bromides, corrosion metals, p-xylene oxidation by-products, and impurities derived as a result of impurities in the p-xylene. The organic bromides may be used as promoters in the oxidation reaction. Examples of corrosion metals are iron and chromium compounds, which inhibit, reduce or entirely destroy the activity of the metal catalyst. Aside from the catalyst and promoter, the oxidizer mother liquor stream also contains by-products and impurities. These by-products and impurities arise partially from minor impurities present in the p-xylene feed stream. Other impurities arise due to the incomplete oxidation of p-xylene resulting in partially oxidized products. Still other by-products result from competing side reactions in the oxidation of p-xylene to terephthalic acid. Carboxylic acids include aromatic carboxylic acids produced via controlled oxidation of an organic substrate. Such aromatic carboxylic acids include compounds with at least one carboxylic acid group attached to a carbon atom that is part of an aromatic ring, preferably having at least 6 carbon atoms, even more preferably having only carbon atoms. Suitable examples of such aromatic rings include, but are not limited to, benzene, biphenyl, terphenyl, naphthalene, and other carbon-based fused aromatic rings. Examples of suitable carboxylic acids include, but are not limited to, terephthalic acid, benzoic acid, p-toluic acid, isophthalic acid, trimellitic acid, naphthalene dicarboxylic acid, 2,5-diphenyl-terephthalic acid and mixtures thereof.

Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 8:1 and about 20:1, and most preferably between about 11:1 and 20:1. Throughout the specification, acetic acid will be referred to as the solvent. However, it should be appreciated that other suitable solvents, such as those disclosed previously, may also be utilized.

In the first step of the present process, the oxidizer purge stream 101 is concentrated by conventional means in a $1^{st}$ evaporator zone 120 comprising an evaporator to produce a $1^{st}$ vapor stream 121 and concentrated purge slurry 122. The evaporator is operated at atmospheric or slightly super atmospheric conditions, generally from about 1 atmosphere to about 10 atmospheres. The vapor stream 121 comprises a majority of the water and solvent, and the concentrated purge stream 122 comprises the remainder of the water and solvent not removed from the oxidizer purge stream 101. The evaporation removes about 50 wt % to about 85 wt % of the solvent mass present in the oxidizer purge stream 101.

Step (b) subjecting the concentrated purge stream 122 and stream 131 comprising water to mix zone 130 to produce a water rich concentrated purge stream 132. The water rich concentrated purge stream 132 is enriched in water in that the weight % water in the water rich concentrated purge stream 132 is greater the concentrated purge stream 122. Any equipment know in the art for mixing two liquid streams can be utilized including mixing the two streams in a pipe equipped with an internal static mixer. In an embodiment of the invention, the feed rate (mass/time) of stream 131 added in mix zone 130 is manipulated to control the weight percent water contained in the downstream super concentrated purge slurry stream 142 from about 5.0 weight percent (wt %) water to about 25 wt % water. Another range to control the water content of stream 142 is from about 8.0 wt % water to about 23.0 wt % water. Yet another range to control the water content of stream 142 is from about 11.0 wt % water to about 21.0 wt % water. In still another range to control the water content of stream 142 is from about 13.0 wt % water to about 19.0 wt % water. The conduit between the $1^{st}$ evaporator 120 and mix zone 130 should be maintained at a temperature at or above 90° C. to minimize solids from coming out of solution in the conduit.

Step (c) subjecting the water rich concentrated purge stream 132 to evaporation in a $2^{nd}$ evaporator zone 140 to produce a $2^{nd}$ vapor stream 141 and a super concentrated purge slurry stream 142. The conduit between mix zone 130 and the second evaporator 140 should be maintained at a temperature at or above 80° C. to minimize the amount of solids coming out of solution in the conduit. The second evaporator zone 140 comprises at least one evaporator operated at vacuum conditions. The evaporation can be conducted at a temperature from about 20° C. to about 90° C.; another range is from about 30° C. to about 80° C. The combination of evaporators 120 and 140 are operated so as to concentrate the oxidizer purge stream 101 to a condition wherein about 75 wt % to about 97 wt % of mass of stream 101 is removed by evaporation. Another range for operation of the combination of evaporators 120 and 140 to concentrate the oxidizer purge stream as represented by stream 101 to a condition wherein about 85 wt % to about 94 wt % of the mass of stream 101 is removed by evaporation. Yet, another range for operation of the combination of evaporators 120 and 140 to concentrate the oxidizer purge stream as represented by stream 101 to a condition wherein about 87 wt % to about 93 wt % of the mass of stream 101 is removed by evaporation.

Step (d) subjecting the super concentrated purge slurry stream 142 and a portion of stream 171 comprising water to $2^{nd}$ mix zone 150 to produce a water rich super concentrated purge slurry stream 152. The water rich concentrated purge slurry stream 152 is enriched in water in that the weight water in the water rich concentrated purge slurry stream 152 is greater than the weight % water in the super concentrated purge slurry stream 142. Any equipment know in the art for mixing two liquid streams can be utilized including mixing the two streams in a pipe equipped with an internal static mixer. The total mass of water in stream 171 routed to mix zones 150 and 170 is controlled such that the ratio of acetic acid:water in stream 172 ranges from about 0.7:1 to about 1.4:1, preferably from about 0.8:1 to about 1.3:1, and most preferably from about 0.9:1 to about 1.2:1. The total mass of stream 171 is divided and routed to mix zone 150 and mix zone 170. The weight percent of stream 171 routed to mix zone 150 can be up to about 25 wt %. The weight percent of stream 171 routed to mix zone 150 can be up to about 50 wt %. The weight percent of stream 171 routed to mix zone 150 can be up to about 75 wt %.

Step (e) comprises filtering a water rich super concentrated purge slurry 152 in a filtration zone 160 to form a filter cake 164 and a mother liquor 163; and Step (f) washing the filter cake 164 with a wash feed 166 in a wash zone 161 to form a washed cake 165 and a wash liquor 167; and optionally dewatering the washed cake 165 in an optional dewatering zone 162 with a gas feed 168 to form a dewatered cake 169. In an embodiment of the present invention, the wash stream 166 comprises water.

In an embodiment of the invention the filtration zone 160 comprises at least one solid liquid separation device. In another embodiment of the invention, the filtration zone and the wash zone can be accomplished in one solid liquid separation device in zone 200. Example of such devices include but are not limited to continuous pressure filters, continuous vacuum filters, batch pressure filters, centrifuges, and like devices. In another embodiment of the invention, the solid liquid separation zone and the wash zone and the optional dewatering zone can be accomplished in one device. Example of such devices include but are not limited to continuous pressure filters, continuous vacuum filters, batch pressure filters, centrifuges, and like devices A suitable pressure filter which can be adapted to the requirements of the instant invented process is a BHS-FEST™, rotary drum pressure filter, although other pressure filters which can accomplish the required operation can be used. Examples of other devices that can used in the solid-liquid separation zone 200 include, but are not limited to; vacuum belt filters, filter presses, centrifuges, pressure leaf filters, pressure drum filters, and vacuum drum filters. The pressure filter can be operated at temperature and pressure sufficient to obtain at least 80 wt % recovery of the metal catalyst from the solute of the mother liquor 163. Preferably the pressure filter can be operated at a temperature of about 25° C. to about 80° C., and a pressure of 2 bar to 6 bar gauge.

Step (g) comprises mixing in $3^{rd}$ mixing zone 170 a portion of water stream 171 with mother liquor stream 163 and optionally a portion of the wash liquor stream 167 to form an aqueous mixture 172. In one embodiment of the invention, the mixing zone 170 comprises a conventional mixer. In an embodiment of the invention, stream 171 comprising water is divided and routed to both the $2^{nd}$ mix zone 150 and the $3^{rd}$ mix zone 170. The total mass of stream 171 routed to mix zones 150 and 170 is controlled such that the ratio of acetic acid:water in stream 172 ranges from about 0.7:1 to 1.4:1 in, preferably from about 0.8:1 to 1.3:1, and most preferably from about 0.9:1 to 1.2:1. It is desirable to keep the aqueous mixture 172 circulating with an external circulation loop. A small amount of extraction solvent 181, generally about 1 to about 10% by weight, preferably less than 5 wt % by weight may be added to the mixing zone 170 to enhance slurry handling by reducing adherence of solids to the side of vessels. This is represented by the dashed arrow from stream 181 in FIG. 1. It is desirable, but not necessary, to subject the aqueous mixture 172, prior to extraction, to a heat treatment at about 60° C. to about 95° C., another range is about 80° C. about 90° C. for about 0.5 to about 4 hours, preferably about 1 to about 2 hours. By this treatment, organic bromides are reacted to yield inorganic bromides which are preferentially retained in the raffinate stream 183. The quantity of bromine-containing compounds purged from the system along with the unwanted impurities is thereby minimized. The heat treatment conserves bromides and simplifies disposal of the organic impurities.

Step (h) comprises contacting an extraction solvent 181 with the aqueous mixture 172 in an extraction zone 180 to form an extract stream 182 and the raffinate stream 183.

The aqueous mixture 172 is fed to an extraction zone 180 wherein the aqueous mixture 172 and the extraction solvent 181 are contacted in the extraction zone 180. The aqueous mixture 172 and the extraction solvent 181 are mixed to form an extract stream 182 comprising solvent, water, organic impurities, and extraction solvent which forms a lighter phase, and the raffinate stream 183 comprising a metal catalyst, corrosion metals, and water. The extract stream 182 is withdrawn as an overhead stream and the raffinate stream 183 is withdrawn from the bottom of extractor in extraction zone 180. In this invention, one embodiment of the extraction zone 180 is a single stage extractor.

The extraction solvent 181 used in the extractor should be substantially water-immiscible to minimize the amount of organic solvent dissolved in the aqueous fraction. Additionally, the extraction solvent 181 is preferably an azeotropic agent which serves to assist solvent recovery from the organic extract. Solvents which have proven to be particularly useful are C1 to C6 alkyl acetates, particularly n-propyl acetate, isopropyl acetate, isobutyl acetate, sec-butyl acetate, ethyl acetate and n-butyl acetate, although other substantially water-immiscible organic solvents having an appropriate density and a sufficiently low boiling point may also be used, such as p-xylene. N-propyl acetate and isopropyl acetate are particularly preferred due to their relatively low water miscibility and excellent azeotropic behavior.

The extraction can be effected using solvent ratios from about 1-4 parts by weight extraction solvent per part aqueous mixture. Although the extraction can be operated at ambient temperature and pressure, heating the solvent and extractor to about 30° C. to about 70° C., another range of about 40° C. to about 60° C. can be used. Although the extract stream 182 comprises small amounts of the metal catalyst and corrosion metals, essentially all of the metal catalyst and the majority of the remaining corrosion metals are contained in the heavier phase, raffinate stream 183.

Step (i) comprises separating the extract stream 182 in a separation zone 190 to form a high boiling point organic impurities stream 192 and a recovered extraction solvent stream 191.

The extract stream 182 comprises organic solvent and organic impurities. The extract stream 182 can further comprises acetic acid and water, often in minor amounts. The extract stream 182 may be distilled in a separation zone 190 comprising conventional distillation equipment. Convention distillation equipment includes, for example, a distillation column.

Most of the organic impurities are extracted by the organic solvent in the extraction zone, 180. This occurs because the organic impurities show a high degree of solubility for the organic solvent and to a lesser extent for acetic acid. By distilling the lighter phase from the extractor, the organic solvent is evaporated allowing the organic impurities to concentrate in the column underflow.

The recovered extraction solvent stream 191 may be recycled to the extractor in the extraction zone 180. The high-boiling organic impurities stream 192 are removed as sludge from the base of the distillation column for disposal.

In an embodiment of the invention, evaporator zones 120, 140, and 150 are operated in a continuous fashion as opposed to batch operation. In an embodiment of the invention, all unit operations (zones 120 to 190) are operated in a continuous fashion as opposed to a batch operation.

EXAMPLES

This invention can be further illustrated by the following examples of other embodiments thereof, although it will be understood that these examples are included merely for purposes of illustration and are not intended to limit the scope of the invention unless otherwise specifically indicated.

Figure 2:
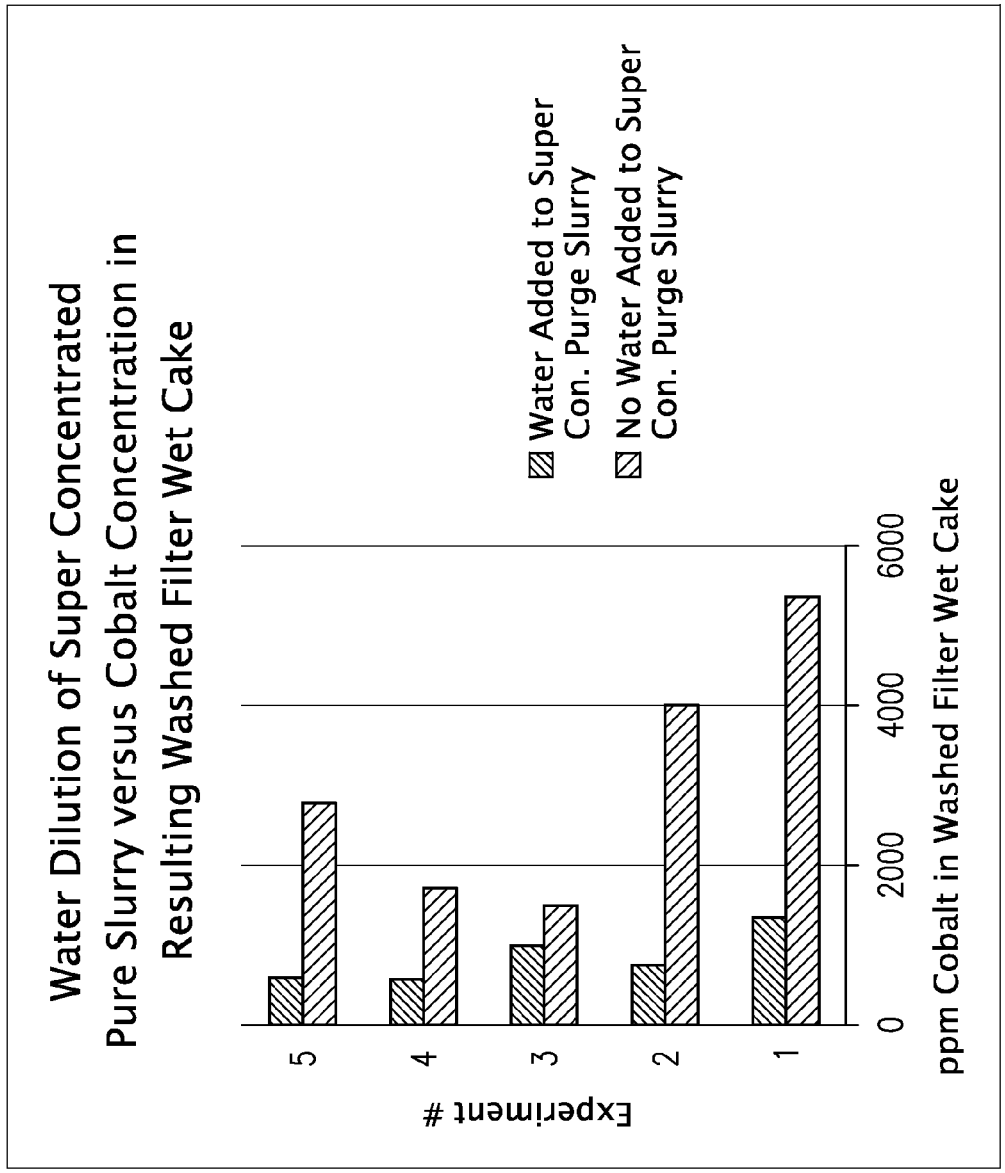
FIG. 2 illustrates how the ppmw (parts per million by weight) cobalt in the filter wet cake is impacted by addition of water to the super concentrated purge slurry just prior to filtration.
Figure 3:
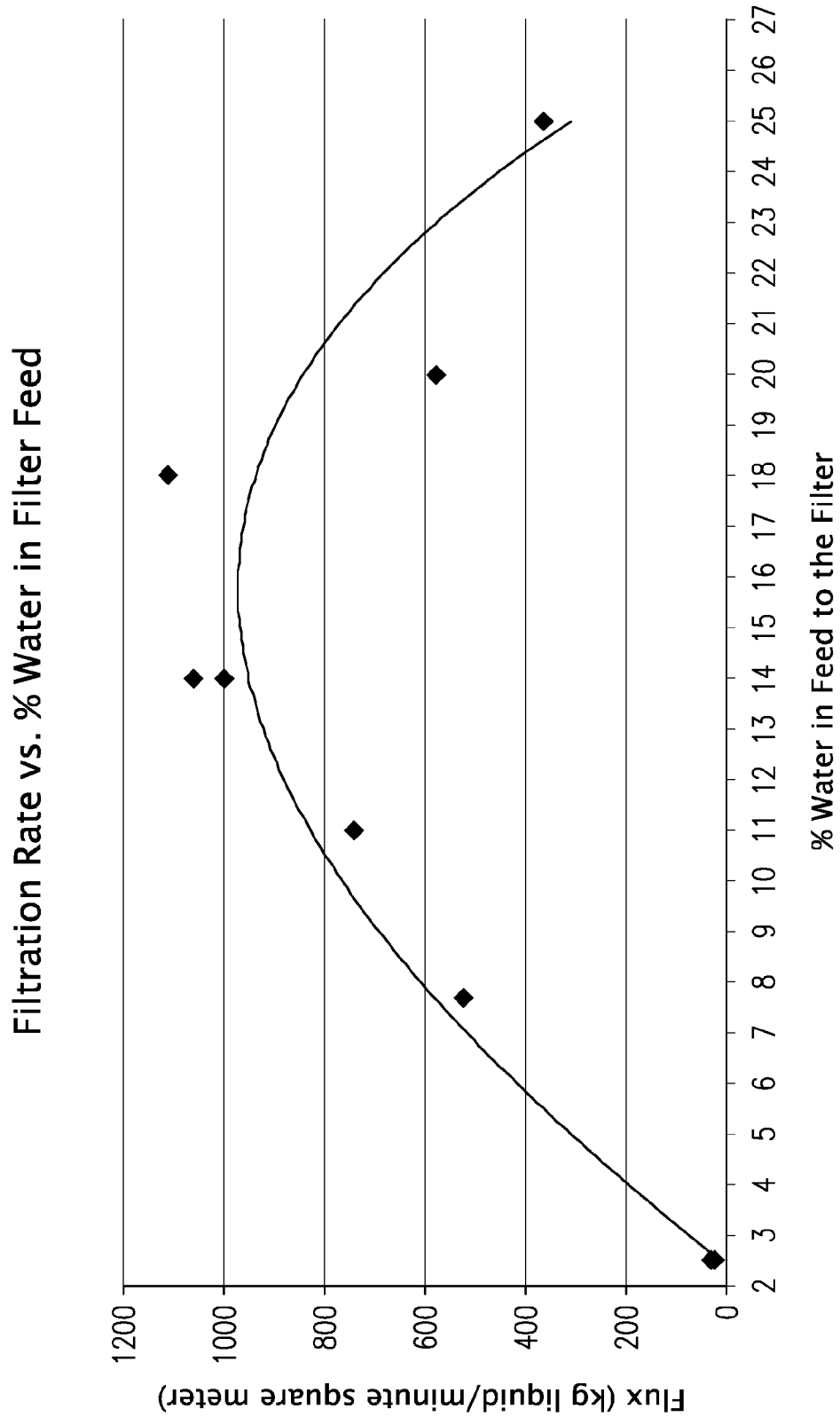
FIG. 3 shows an embodiment of the invention wherein the filtration rate of the feed to the filter is impact by weight % water in the super concentration purge slurry stream.

The data for Examples 1 through 5 is outlined in Table 1 and FIG. 2 was generated in a laboratory. An objective of these examples is to illustrate the benefit of adding water to super concentrated purge slurry stream 142 prior to filtration on cobalt recovery in the filter. The addition of water to super concentrated purge slurry stream 142 results in a decrease in the cobalt concentration in the washed filter cake stream 165 and less cobalt lost in the purge process. Cobalt present in stream 165 is not recycled to the terephthalic acid oxidation zone where the cobalt functions as a catalyst.

For each laboratory experiment, oxidizer purge feed 101 was obtained from a commercial plant comprising about 6% water and 94% acetic acid. 75% of the mass of oxidizer purge feed was removed by evaporation at 120° C. in a $1^{st}$ evaporator zone resulting in a concentrated purge stream 122 comprising about 4.6% water. 120° C. concentrated purge stream 122 was mixed continuously in a mix zone with varying amounts of ambient temperature water and then subjected to additional evaporative concentration at a final temperature of about 55° C. resulting in super concentrated purge stream 142 comprising water ranging from about 8 weight percent (wt %) to 25 wt %. About 92 wt % of the original mass of the oxidizer purge feed is lost during evaporative concentration. For each of the 5 experiments, super concentrated purge stream 142 is divided into two parts. One part of stream 142 is filtered. The other part of stream 142 is mixed with water generating a water rich super concentrated purge stream 152 and then filtered. It is illustrative to compare the concentration of trated purge slurry 152. The amount of water from stream 171 is added in the $2^{nd}$ mix zone to minimize the amount of cobalt in the wet cake 165. In another embodiment of the invention, the amount of water from stream 171 is added in the $2^{nd}$ mix zone such that the amount of cobalt in the washed filter cake 165 is less than 1500 ppmw (parts per million by weight). In another embodiment of the invention, the amount of water from stream 171 is added in the $2^{nd}$ mix zone such that the amount of cobalt in the wet cake 165 is less than 1000 ppmw (parts per million by weight). In another embodiment of the invention, the amount of water from stream 171 is added in the $2^{nd}$ mix zone such that the amount of cobalt in the washed filter cake 165 is less than 600 ppmw (parts per million by weight).

Third, it clear that the filtration rate of streams 142 and 152 for each experiment are not materially different. Therefore, even though the addition of water in the first mix zone 130 has a material impact on filtration rate of downstream slurries, the addition of water in the $2^{nd}$ mix zone 150 has no material impact on downstream slurry filtration rate. The motivation for adding water in the $2^{nd}$ mix zone is to generate a water rich super concentrated purge slurry 152 that upon filtration will result in a filter cake with lower cobalt concentration relative to it respective upstream super concentrated purge slurry 142.

TABLE 1

Experimental Filtration Data for Super Concentrated Purge Slurry With and With Out Water Addition in Mix Zone 150

| Expt. # | Zone 140 2nd Evaporator Wt. % Water in Stream 142 (SCPS) | Zone 150 2nd Mix Zone | | Zone 160 Filtration Zone | | | | Zone 161 Wash Zone | | Stream 165 |
|---|---|---|---|---|---|---|---|---|---|---|
| | | Stream 142 Mass (g) | Stream 171 Mass (g) | Stream 152 Feed (g) | Filtration Time (sec) | Stream 163 M. Liquor (g) | Flux g liquid time (g/sec) | Stream 166 Wash (g) | Stream 167 W. Liquor (g) | Wet Cake Cobalt (ppm) |
| 1 | 7.7% | 401 | 0 | 401 | 16 | 306 | 25 | 76 | 133 | 5,371 |
| | 7.7% | 400 | 243 | 643 | 28 | 572 | 23 | 76 | 120 | 1,351 |
| 2 | 11% | 400 | 0 | 400 | 13 | 322 | 31 | 98 | 150 | 3,991 |
| | 11% | 400 | 226 | 626 | 19 | 583 | 32 | 98 | 107 | 743 |
| 3 | 18% | 400 | 0 | 400 | 8 | 313 | 50 | 140 | 201 | 1,484 |
| | 18% | 400 | 152 | 552 | 12 | 464 | 46 | 140 | 198 | 979 |
| 4 | 20% | 400 | 0 | 400 | 18 | 351 | 22 | 65 | 102 | 1,719 |
| | 20% | 400 | 255 | 655 | 23 | 623 | 29 | 65 | 67 | 567 |
| 5 | 25% | 400 | 0 | 400 | 27 | 324 | 15 | 117 | 168 | 2,787 |
| | 25% | 400 | 199 | 599 | 41 | 566 | 15 | 117 | 125 | 591 | cobalt in the washed filter cakes generated by filtering the concentrated purge slurry stream 142 and the water rich concentrated purge slurry 152. Filtrations were accomplished in a lab scale pressure filter operated at 3 bar pressure gauge with filtration area of 20 cm$^2$, washed with water, and dewatered with N$_2$. In all experiments about 10 grams of wash was used each gram of dry solids in the wet cake.

At least three conclusions can be drawn from the experimental data in Table 1.

First, it is clear that the concentration of cobalt in the washed filter cakes 165 generated by filtering water rich super concentrated purge stream 152 is much less than the concentration of cobalt in the washed filter cakes 165 generated by filtering super concentrated purge stream 142 for each experiment.

Second, it is clear that the addition of water stream 131 to a concentrated purge stream 122 in a first mix zone 130 has a material impact on the filtration rate of the downstream super concentrated purge slurry 142 and water rich super concen-

I claim:

1. A terephthalic acid purge process comprising:
    (a) subjecting an oxidizer purge stream formed in a terephthalic acid process to evaporation in a $1^{st}$ evaporator zone to produce a $1^{st}$ vapor stream and a concentrated purge stream; wherein said oxidizer purge stream comprises a carboxylic acid, a metal catalyst, impurities, water and a solvent; wherein said solvent comprises acetic acid and water;
    (b) adding water to said concentrated purge stream in a $1^{st}$ mixing zone to produce a water rich concentrated purge stream;
    (c) subjecting said water rich concentrated purge stream to evaporation in a $2^{nd}$ evaporator zone to produce a $2^{nd}$ vapor stream and a super concentrated purge slurry stream; and
    (d) adding water to the super concentrated purge slurry stream in a $2^{nd}$ mix zone to produce a water rich super concentrated purge slurry, and (e) filtering said water rich super concentrated purge slurry in a solid-liquid separation zone to form a filter cake and mother liquor;

(f) washing said filter cake with a wash feed in said solid-liquid separation zone to form a washed filter cake, and wash liquor; and (g) adding water to said mother liquor in a $3^{rd}$ mix zone and subjecting an aqueous mixture so formed to extraction with an extraction solvent to produce an extract stream and a raffinate stream comprising the metal catalyst.

2. The process according to claim 1 wherein the mass of water combined in steps (d) and (g) results in said aqueous mixture in step (g) with acetic acid:water mass ratio ranging from 0.7:1 to 1.4:1.

3. The process according to claim 1 wherein the mass of water combined in steps (d) and (g) results in said aqueous mixture in step (g) with acetic acid:water mass ratio ranging from 0.9:1 to 1.2:1.

4. The process according to claim 1 wherein the mass of water combined in $2^{nd}$ mix zone step (d) ranges from about 5 weight % to 25 weight % of the total mass of water combined in the $2^{nd}$ mix zone step (d) and the $3^{rd}$ mix zone step (g).

5. The process according to claim 1 wherein the mass of water combined in $2^{nd}$ mix zone step (d) is ranges from about 5 weight % to 50 weight % of the total mass of water combined in the $2^{nd}$ mix zone step (d) and the $3^{rd}$ mix zone step (g).

6. The process according to claim 1 wherein the mass of water combined in $2^{nd}$ mix zone step is in sufficient quantity such that the washed filter cake contains cobalt in an amount less than 1500 ppm.

7. The process according to claim 6 wherein at least 80% of said metal catalyst from said super concentrated purge slurry is recovered through said separation zone into said mother liquor and said wash liquor cumulative.

8. The process according to claim 7 wherein about 75% to about 95% of said oxidizer purge stream mass is removed by evaporation from said oxidizer purge stream in steps (a) and (c) combined.

9. The process according to claim 8 where in at least a portion of the washed filter cake is routed to the terephthalic acid product downstream of an oxidation zone.

10. The process according to claim 1 wherein said super concentrated purge slurry has a water content of about 8 wt % to about 23%.

11. The process according to claim 1 wherein said super concentrated purge slurry has a water content of about 11 wt % to about 21%.

12. The process according to claim 1 wherein said super concentrated purge slurry has a water content of about 13 wt % to about 19%.

13. The process according to claim 12 wherein said solid liquid separation device is a pressure filtration device that operates at a temperature between about 25° C. to about 90° C.

14. The process according to claim 13 wherein said pressure filtration device comprises at least one filter cell and wherein at least one filter cell accumulates at least 0.25 inch in depth of said filter cake.

15. The process according to claim 14 in which at least a portion of the mother liquor formed in step (e) is routed back to the oxidation zone of the terephthalic acid process.

16. The process according to claim 15 wherein said pressure filtration device is a rotary pressure drum filter.

17. The process according to claim 16 wherein the residence time in the second evaporation zone ranges from 30 minutes to 180 minutes.

18. The process according to claim 1 wherein the extract stream is routed to a distillation column to recover the extraction solvent and a waste sludge stream comprising oxidation by-product impurities.

19. The process according to claim 18 in which the solvent is acetic acid mixed with water, in a ratio of 8:1 and about 20:1.

20. The process according to claim 19 in which the mass of water added in the $1^{st}$ mix zone is manipulated to control the weight percent of water contained in the downstream super concentrated purge slurry stream from 5 wt % to 25 wt % water.

21. The process according to claim 18, in which the solvent is acetic acid mixed with water, in a ratio of 11:1 and about 20:1.

22. The process according to claim 1 in which the mass of water added in the $1^{st}$ mix zone is manipulated to control the weight percent water contained in the downstream super concentrated purge slurry stream from 10 wt % to 20 wt % water.

23. The process according to claim 1 in which the mass of water added in the $1^{st}$ mix zone is manipulated to control the weight percent water contained in the downstream super concentrated purge slurry stream from 13 wt % to 18 wt % water.

24. The process according to claim 1 in which the mass of water added in the $1^{st}$ mix zone is manipulated to control the weight percent water contained in the downstream super concentrated purge slurry stream from 8 wt % to 23 wt % water.

* * * * *